US011357898B1

(12) United States Patent
Tamari (10) Patent No.: US 11,357,898 B1
(45) Date of Patent: Jun. 14, 2022

(54) HYBRID VENOUS RESERVOIR

(71) Applicant: Yehuda Tamari, Oyster Bay, NY (US)

(72) Inventor: Yehuda Tamari, Oyster Bay, NY (US)

(*) Notice: Subject to any disclaimer, the term of this patent is extended or adjusted under 35 U.S.C. 154(b) by 0 days.

(21) Appl. No.: 17/231,697

(22) Filed: Apr. 15, 2021

(51) Int. Cl.
*A61M 1/36* (2006.01)

(52) U.S. Cl.
CPC ........ *A61M 1/3632* (2014.02); *A61M 1/3638* (2014.02); *A61M 1/3666* (2013.01); *A61M 2205/0216* (2013.01); *A61M 2205/7527* (2013.01)

(58) Field of Classification Search
CPC .............. A61M 1/3632; A61M 1/3638; A61M 1/3666; A61M 2205/0216; A61M 2205/7527
See application file for complete search history.

(56) References Cited

U.S. PATENT DOCUMENTS

| 7,591,812 | B1 | 9/2009 | Tamari |
| 8,147,440 | B2 | 4/2012 | Tamari |
| 8,882,696 | B2 | 11/2014 | Tamari |

OTHER PUBLICATIONS

Medtronic Affinity reservoir catalog.
LivaNova (Sorin) Inspire reservoir catalog.
Terumo CAPIOX reservoir catalog.
Spectrum Sensor Module with 3 flow meters.

*Primary Examiner* — Leslie R Deak

(57) ABSTRACT

The invention is an innovative hybrid venous reservoir designed to receive and store blood during cardiopulmonary bypass (CPB), the hybrid venous reservoir consisting of an air purging chamber that limits air in the venous blood entering the air purging chamber from exiting the air purging chamber in combination with a compliant storage chamber with at least one pliable wall, the combination providing a large volume capacity while limiting the area of the blood-air interface to that of the air purging chamber.

19 Claims, 6 Drawing Sheets

Present HVR

Fig. 1c Present HVR

Fig. 1b Prior Art HVR

HYBRID VENOUS RESERVOIR

BACKGROUND OF THE INVENTION

Field of the Invention

Figure 1A:
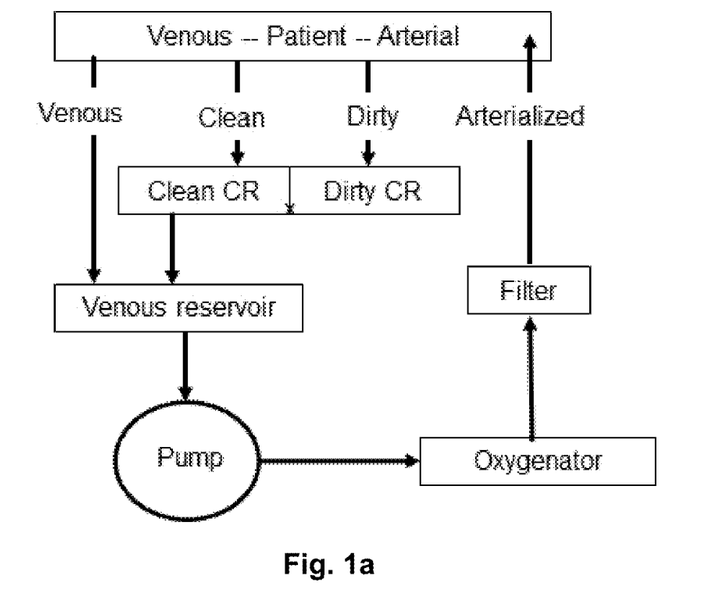
FIG. 1a is a line drawing of the pertinent components of a typical cardiopulmonary bypass circuit.

Venous reservoirs are an essential component of the cardiopulmonary bypass (CPB) circuit adopted to support patients by the heart lung machine. FIG. 1a is a line drawing summarizing the different components of a CPB circuit. As shown, blood flows from the venous side of the patient to a venous reservoir and then is pulled from the reservoir by an arterial pump that pushes the blood to an oxygenator, then through an arterial filter and finally back to the arterial side of the patient. Blood collected from the surgical field ("dirty" blood) and from the circuit or patient ("clean" blood) must be debubbled and filtered prior to returning it back to the patient. The latter is accomplished by a cardiotomy reservoir shown as "CR" in FIG. 1a. The venous reservoir serves to trap and remove air bubbles from venous blood flowing into it and provide volumetric compliance to accommodate variations in the blood volume circulating in the extracorporeal circuit and the patient during CPB. The present hybrid venous reservoir (HVR) has a small but significant change that improves, while retaining many of its advantages, of Tamari's HVR described in U.S. Pat. Nos. 7,591,812, 8,147,440, and 8,882,696, the disclosures of these patents being incorporated herein by reference thereto.

Description of the Prior Art

Blood flowing from the venous side of the patient to a venous reservoir depends on the resistance of the fluid conduit between the patient and the reservoir and the height of the patient above the reservoir. The resulting flow is referred to as gravity drainage. Vacuum assisted venous drainage (VAVD) overcomes the flow limitations of gravity drainage by applying vacuum to the venous reservoir thereby increasing the pressure difference between the patient and the venous reservoir. VAVD allows for a decrease in the inner diameter (ID) of the venous line from the patient to the reservoir, thereby reducing prime volume and enabling the use of a cannula with a smaller ID, and hence a smaller outside diameter (OD), which translates to an easier insertion, better surgical view and a smaller surgical incision. The present HVR, as other prior art venous reservoirs, allows for VAVD.

Tamari's U.S. Pat. No. 7,591,812 describes a hybrid venous reservoir that combines an air purging chamber combined with a compliant storage chamber (CSC), the CSC comprised of a flexible wall and a rigid wall to form a "closed" variable blood chamber that allows VAVD, (see Abstract and FIG. 4d of U.S. Pat. No. 7,591,812). That reservoir teaches a design that prevents it from emptying completely and air from reaching the blood pump by passively shutting off the HVR outlet port (see its claim 50). This reservoir is inherently the safest venous reservoir. However, the "shut-off" design requires additional volume (see FIG. 5a of Tamari's U.S. patent '812). As shown, outlet 6 of compliant storage chamber 1103 shuts off before air in purging chamber 1116 reaches the outlet of compliant storage chamber 1103. This design requires additional volume to prime and operate. The additional volume is due the volume required to fill in long channel 4b, inlet 5 of the closed chamber 1103 as well as the volume in the air purging chamber correspond to the level of the outlet of the closed chamber (see "y1" in FIG. 4a of Tamari's U.S. patent '812 or below line B-B' of FIG. 1b of the present HVR). In addition, the flow from APC 1116 to compliant chamber 1103 is by gravity and requires the ID of channel 4b to have low resistance to flow. Experience has shown that a ⅝" ID tubing suffices. However, a ⅝" ID tubing requires a larger volume to fill than a smaller ID tube used when blood is drawn by a pump, as is the case for state-of-the-art hardshell venous reservoirs and the present HVR.

During VAVD applications it is necessary to trap water vapor in the air exhausted from the HVR that condenses on the cooler walls of the vacuum tubing (not shown) to prevent that condensate from dripping back into the blood. Tamari's U.S. Pat. No. 8,147,440 describe a venous reservoir incorporating a vapor trap. (See FIG. 9b item 908 and claim 1.) The present HVR also incorporates a vapor trap.

During CPB "clean" blood includes blood aspirated from a venting site (e.g., the aortic root cardioplegia cannula, LV vent, arterial filter). Clean blood is distinctly different from "dirty" blood sucked from the surgical field, mostly of which comes from the pericardial sack. Clean blood may entrain a large volume of air. If that blood is added directly to venous blood it generates a large volume of foam with its concomitant large blood-gas area. Thus, before clean blood is returned to the patient, its entrapped air must be removed. Before sucker blood can be returned it must be filtered to remove both debris (e.g., particles of fat, tissue, clots, bone wax) and entrapped air. However, filtered retransfusion of "dirty" blood increases postoperative systemic inflammatory response, hemolysis, acellular lipid deposits in the microvasculature, thrombin, neutrophil, platelet activation, and the release of neuron-specific enolase. It is therefore preferable to send dirty blood to a cell saver for processing. That is not the case for the clean blood. Once defoamed and deaerated it can be returned to the venous blood. It is therefore clinically useful for clean and dirty blood for each to be processed by a separate chamber, avoiding the clean blood from being exposed to the dirty blood with its aforementioned deleterious consequences. Hence a two-chamber cardiotomy resolves that issue. Tamari's U.S. Pat. No. 8,882,696 describes an HVR with a clean chamber and a dirty chamber separated by a common wall. See FIG. 5a chambers 1115a and 1115b and claim 1). A two-chamber cardiotomy is also featured in the present HVR.

Air interfacing with blood can denature blood protein, hence minimizing the area of the blood-to-air (blood-air) interface is a major design objective of devices used in CPB circuits. The HVR taught by Tamari's U.S. Pat. No. 7,591,812 achieves that by limiting the blood-air interface to the air purging chamber while providing an additional volume capacity in the air free compliant storage chamber. (See FIG. 8a of Tamari's U.S. patent '812). The present HVR minimizes the blood-air interface using the same design.

State of the heart lung machines used for CPB, such as that of Spectrum Medical, incorporate numerous flowmeters that measure and monitor both the flow into the venous reservoir (venous flow) and the flow out of the venous reservoir (arterial pump flow). With these systems, the arterial pump flow can be automatically adjusted to match to the venous inflow. Such systems, and in addition the arterial pump responding to a signal from a detector monitoring the blood level in the reservoir, can match the safety inherent in the passive shut-off feature of Tamari's '440, '696 and '812 but without the additional prime and operating volume required for that prior art HVR.

Figure 1B:
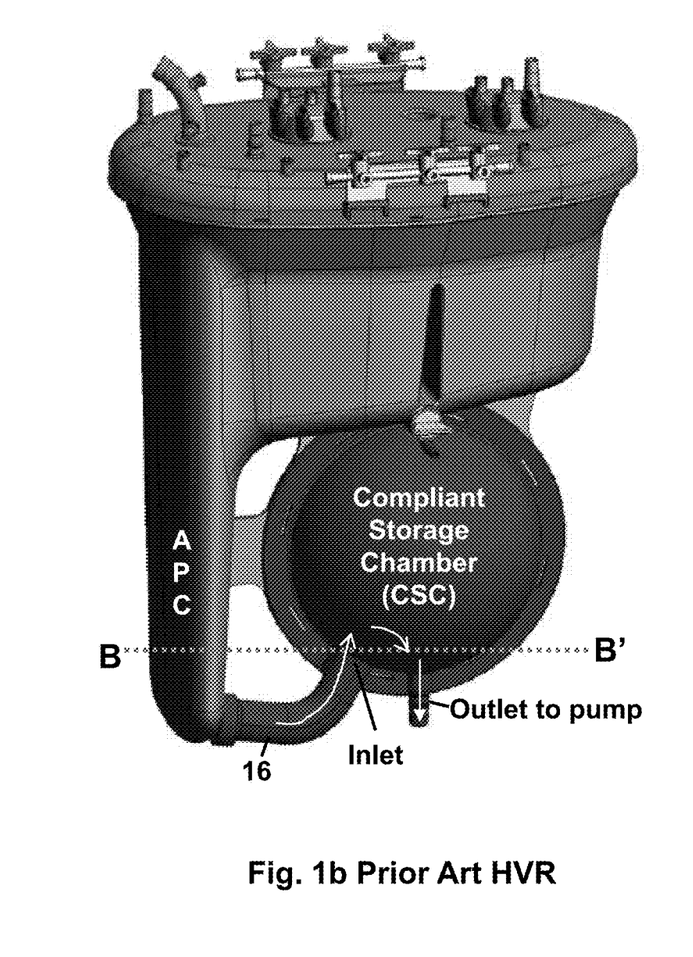
FIG. 1b is a drawing illustrating a typical HVR as taught by Tamari's earlier patents.
Figure 1C:
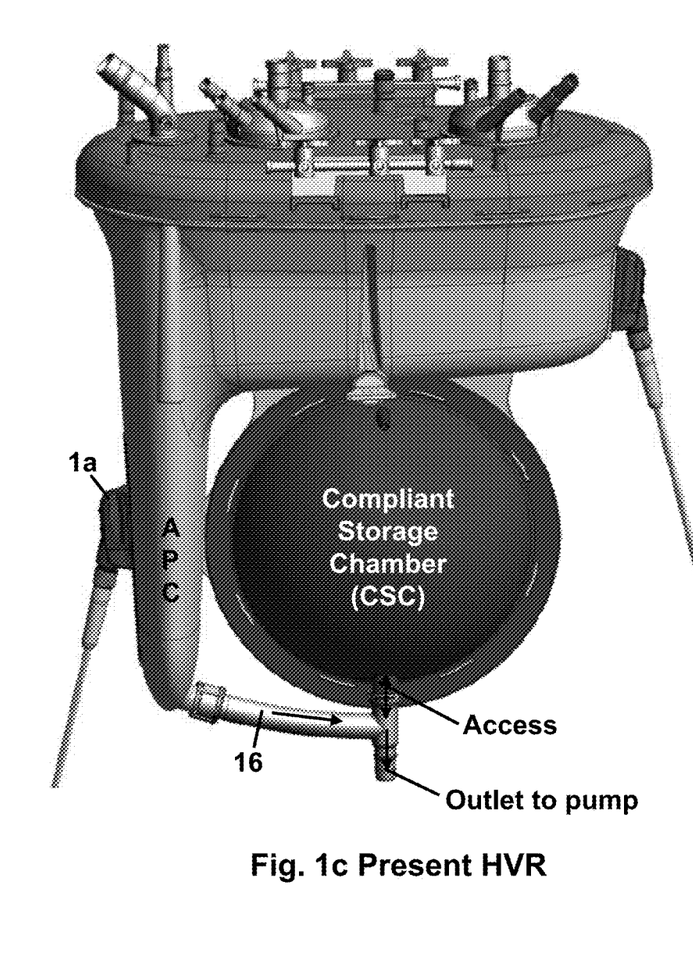
FIG. 1c is a drawing illustrating an embodiment of the present HVR.

The present HVR incorporates all the features taught by Tamari's U.S. patents '812, '440, and '696 except for its fluid communication from the APC to the CSC. The difference is illustrated by comparing FIG. 1b showing an HVR according to prior art to FIG. 1c illustrating the present HVR. With Tamari's prior art reservoir, at the end of the case the volume below line B-B' remains in the reservoir. See FIG. 1b. The present HVR, shown in FIG. 1c, can be emptied completely.

BRIEF SUMMARY OF THE INVENTION

The HVR consists of a blood chamber that traps and inhibits air in the venous blood entering it from exiting it. The chamber has a small horizontal cross-sectional area and is referred to as the air purging chamber (APC). The APC described in detail in Tamari's U.S. patents numbers '812, '440, and '696 consists of two blood chambers: an inlet chamber with an inlet and an outlet chamber with an outlet. The two-chambers have a screen as a common wall and a common air exhaust port. Venous blood enters the inlet chamber and flows across the screen to the outlet chamber. Air bubbles entering the inlet chamber are inhibited from crossing the screen and are retained in the inlet chamber where they are purged to atmosphere via the air exhaust port. Thus, the APC separates air bubbles from the venous blood and purges that air to atmosphere as is the case with the hard-shell venous reservoir but without the need for the suction or vacuum required with prior state-of-art soft-shell venous reservoirs. A defoamer, located at the top of the inlet chamber, collapses foam that forms by the air bubbles in the blood. Combining the APC with a two-chamber cardiotomy reservoir and a compliant storage chamber having at least one flexible wall as a single unit provides a venous reservoir with unique clinical advantages as described by Tamari's U.S. patents '812, '440, and '696 and are articulated below.

Tamari's U.S. Patents '812, '440, and '696 teach of a venous reservoir that:
combines an APC with a compliant storage chamber that limits the area of the blood-air interface to that of the APC;
incorporates a vapor trap;
in one permutation, has a two-chamber cardiotomy reservoir: one for processing "clean" blood; the other for processing "dirty" blood;
allows vacuum assisted venous drainage (VAVD);
inherently and passively prevents air from exiting the HVR.

Feature 5 described in reference to FIG. 5a of patent '440 requires blood to flow from outlet 4 of air purger chamber 1116 to inlet 5 of compliant storage chamber 1103 via fluid communication 4b. That flow is by gravity and requires a large ID (e.g., ⅝") and must flow through CSC 1103. See FIG. 4a of aforementioned U.S. Pat. No. 7,591,812. With the current invention venous blood is pulled from the APC by pump 20 via conduit 16 and does not flow through the CSC. See FIG. 1c. In addition, the present HVR eliminates inlet 5 of prior art shown in FIG. 1b and allows for complete emptying of the reservoir at the end of the case when the patient is taken off CPB. In Tamari's aforementioned earlier patents, the venous reservoir retains the volume in the reservoir below line B-B' shown in FIG. 1b and height y1 in FIG. 4a of aforementioned U.S. Pat. No. 7,591,812.

It is the objective of the present HVR to utilize the unique features of the venous reservoir according to Tamari's U.S. Pat. Nos. 7,591,812, 8,147,440, and 8,882,696 but reduce its prime volume, its operating volume and allow it to empty completely at the end of the case.

BRIEF DESCRIPTION OF THE DRAWINGS

The figures below describe the functionality of the present HVR in the simplest form and are only for illustrative purposes. The figures are not necessarily conducive to manufacturing a clinical unit; that can be accomplished by a variety of established means.

FIG. 4b is a 3-D view depicting a frontal view of the present HVR shown in FIG. 4a.

DETAILED DESCRIPTION OF THE INVENTION

Reference should now be made to the drawings wherein the same reference numerals are used throughout to designate the same or similar parts. It should be noted that the use of cardiopulmonary bypass, as shown in FIG. 1a is for descriptive purposes and should not be taken as a limitation to the use of the device described hereinafter and is only for illustrative purposes. Other embodiments are possible and, therefore, what follows is suggestive of the art and should not be construed as a limitation of the scope or the spirit of the invention.

FIG. 1a is a schematic representation of a typical cardiopulmonary bypass circuit as routinely practiced. Here blood flows from the venous side of a patient placed on CPB into a venous reservoir used to store venous blood and eliminate air entrapped in the venous blood. The blood is pumped from the reservoir through an oxygenator (i.e., an artificial lung) that removes $CO_2$ and adds $O_2$ and onward through an arterial filter and back to the arterial side of the patient. The aforementioned "clean" and "dirty" blood is directed to the clean chamber and dirty chamber, respectively, of a two-chamber cardiotomy.

FIG. 1b shows conduit 16 forming the fluid communication between the air purging chamber and the compliant storage chamber for a venous reservoir according to Tamari's prior art. The volume in this reservoir below line B-B' is minimum volume required to use the reservoir and the volume remaining in the reservoir when the circuit is emptied at the end of the case.

FIG. 1c shows conduit 16 forming the fluid communication between the air purging chamber and the compliant storage chamber of the present HVR. The innovation is illustrated by comparing the prior art HVR illustrated in FIG. 1b to the present HVR illustrated in FIG. 1c. The embodiment of the present HVR allows it to be emptied completely while the prior art HVR retains the blood volume below line B-B'.

Figure 2:
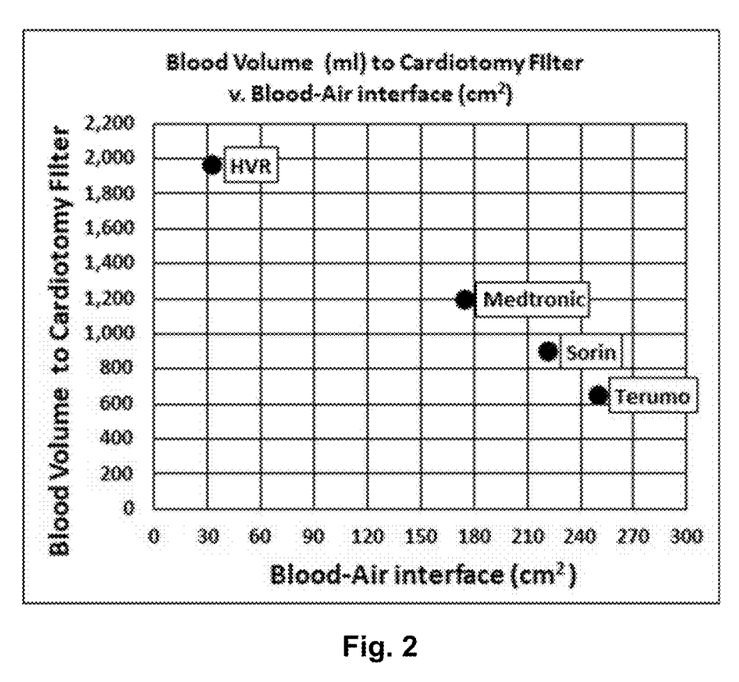
FIG. 2 is a graph illustrating the blood-air interface area of current reservoirs and the present HVR when the blood volume in the reservoirs contacts the cardiotomy filter.

FIG. 2 compares the volume in the venous reservoir at which the venous blood contacts the cardiotomy filter of three current venous reservoirs designed for adult patients (e.g., Terumo CAPIOX, Sorin (LivaNova) Inspire, Medtronic Affinity) to one embodiment of the current HVR, each having a nominal volume capacity of 4,500 ml. Also shown is the blood-air interface (cross sectional area of the reservoir at that volume). It is clear that the HVR, as taught by Tamari's U.S. Pat. No. 7,591,812 FIG. 8a, in general, also provides a significant lower blood-air interface area. For example, at a volume of 1,500 ml, the HVR expose the blood to a blood-air interface area of 33 $cm^2$ whereas the other reservoirs' area is over 175 $cm^2$ and as high as 300 $cm^2$.

Figure 3A:
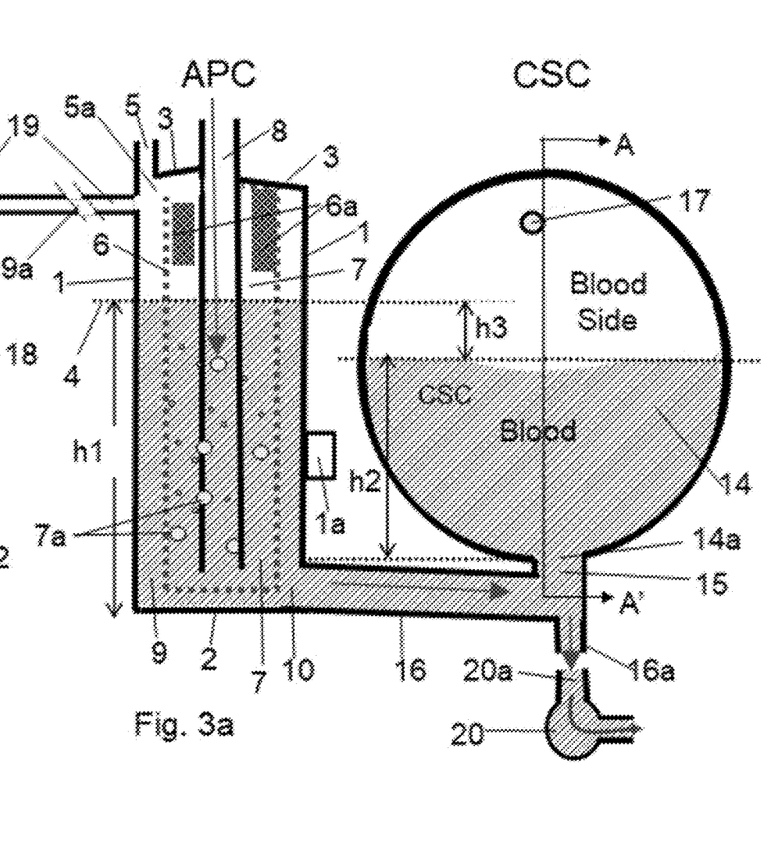
FIG. 3a is a line drawing illustrating a front view of one embodiment of an air purging chamber in combination with a compliant storage chamber.
Figure 3B:
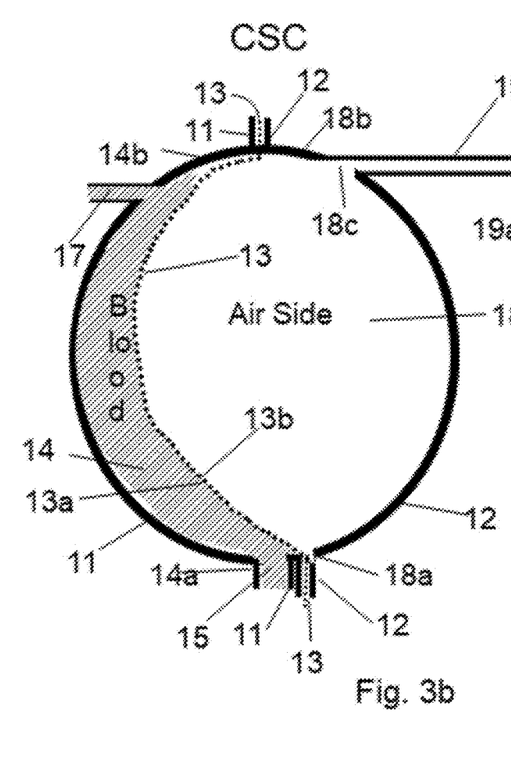
FIG. 3b is a line drawing illustrating a side view of FIG. 3a taken along A-A'.

FIG. 3a is a line drawing of a front view and FIG. 3b is a line drawing of a view along A-A' in FIG. 3a illustrating an embodiment of the present HVR. The present HVR includes an APC defined by outer vertical wall 1 defining outlet chamber 9, a first bottom 2, a first top 3 and a first outlet 10 located along bottom 2. The APC is adapted to contain blood and air wherein interface 4 between the blood and the air (i.e., blood-air interface) occurs at first height h1. First height h1 is measured from first bottom 2 and has horizontal cross-sectional area A1 at height h1. The APC also includes first air exhaust port 5 located along first top 3 in fluid communication with ambient atmosphere through which air in the venous blood entering the APC is exhausted. The APC also includes screen 6 that divides the APC into inlet chamber 7 having first inlet 8 and defining the inner wall of outlet chamber 9. Screen 6 provides fluid communication between first inlet 8 and first outlet 10 and hinders air bubbles 7a in the venous blood entering inlet chamber 7 from reaching first outlet 10. Foam generated in inlet chamber 7 is defoamed and collapsed by defoamer 6a. Fluid communication 5a along top 3 between inlet chamber 7 and outlet chamber 9 assures the pressure in each of the two chambers is the same. Fluid communication 5a also assures air in either chambers can exhaust via first air exhaust port 5. As designed, air in the venous blood entering inlet chamber 7 rises to first height h1 from where it is purged to ambient atmosphere via first air exhaust port 5. Preferably the maximum cross-sectional blood-air interface area A1 anywhere along first height h1 is less than 40 $cm^2$.

The present HVR limits the blood-air interface area to A1 of the APC; while compliant storage chamber 14 (CSC 14) provides a large air-free volume capacity. This feature is also part of aforementioned Tamari's patents.

FIG. 3b is a line drawing of a cross section along A-A' of FIG. 3a. It illustrates a dual chamber structure comprised of second rigid wall 11, third rigid wall 12 and diaphragm 13; the structure is adapted to contain venous blood. Diaphragm 13 is compatible with blood, has a pliable wall, such as polyurethane or silicone, and is defined by its blood side 13a and air side 13b. Diaphragm 13 is sandwiched and sealed along its periphery between the peripheries of second rigid wall 11 and third rigid wall 12 thereby forming two-chambers: CSC 14 and air chamber 18. Second rigid wall 11, third rigid wall 12 and diaphragm 13 are preferably hemispherical in shape and match each other to form a rigid outer spherical chamber having variable volume CSC 14 and variable volume air chamber 18. Preferably the outer periphery of diaphragm 13 facilitates the seal between the blood side 13a of diaphragm 13 and the second rigid wall 11 and/or between air side 13b of diaphragm 13 and the third rigid wall 12.

CSC 14 has second bottom 14a, second top 14b and a first access 15 fitted along second bottom 14a, forming fluid communication with CSC 14. Preferably the shape of diaphragm 13 is such that it can nestle and mate against second rigid wall 11 to allow CSC 14 to empty completely. Conduit 16 provides a fluid communication for venous blood to flow from outlet chamber 9 via outlet 10 to CSC 14 via first access 15. Outlet port 16a is in fluid communication with conduit 16 assuring fluid communication between outlet chamber 9, CSC 14 and inlet 20a of arterial pump 20. When venous and pump flow stop, then blood level h2 in CSC 14 equals blood level h1 in APC.

FIG. 3b also illustrates air chamber 18 defined by the space formed between third rigid wall 12 and air side 13b of diaphragm 13, the two walls sealed along their corresponding peripheries. Air chamber 18 has a third top 18b and third bottom 18a. Third rigid wall 12 incorporates air access 18c that provides fluid communication with first air chamber 18. It is crucial that diaphragm 13 moves freely to accommodate changes in blood volume in CSC 14 such that the pressure in CSC 14 is preferably within 5 mmHg of the pressure in air chamber 18.

To allow for aforementioned VAVD application, the vacuum applied to first air exhaust port 5 must be applied equally to inlet chamber 7, outlet chamber 9 and to air chamber 18. Vacuum applied to air chamber 18 is transmitted to the blood in CSC 14 across diaphragm 13. To that end, first fluid path 19 is added to form a fluid communication between air chamber 18 and first air exhaust port 5 of the APC. Thus, the present HVR can operate whether first air exhaust port 5 is open to atmosphere or is connected to a regulated vacuum source. Also shown is second fluid path 5a forming a direct fluid communication between the top of inlet chamber 7, first outlet chamber 9 and first air exhaust port 5. It should be noted, and as indicated by break 19a, first fluid path 19 is shown only for illustrative purpose and can be made in a variety of ways.

To maximize emptying the present HVR at the end of the case, first outlet 10 should be slightly higher than second outlet 16a such that conduit 16 is on a slight down incline towards second outlet 16a.

The functionality of the present HVR is elucidated by the example below.

As the present HVR is primed with crystalloids/blood, the prime flows into inlet chamber 7 via first inlet 8. The prime, but not air bubbles 7a, flows across screen 6 into outlet chamber 9 and into conduit 16 via outlet 10 to fill CSC 14 via first access 15. Air bubbles 7a rise to blood-air interface h1 and are exhausted via first air exhaust port 5. As CSC 14 fills, air present in CSC 14 is withdrawn/expelled via port 17 preferably positioned along second top 14b located on second rigid wall 11 and preferably being a Luer fitting accommodating a stopcock (not shown). Once on bypass, venous blood enters inlet chamber 7 via first inlet 8, crosses screen 6 into outlet chamber 9 and exits via first outlet 10. Air 7a in the incoming venous blood, hindered from crossing screen 6, floats upward to level h1 where it coalesces with the air above blood-air interface h1 and is purged via first air exhaust port 5. Foam formed by the air percolating with the blood in inlet chamber 7 is collapsed and defoamed by defoamer 6a located along the top of inlet chamber 7. The air-free venous blood exits first outlet 10 to enter conduit 16 from where it can exit via second outlet 16a and pulled by and into arterial pump 20.

If the venous blood flowing into inlet chamber 7 is greater than the flow generated by pump 20, then the volume difference between the venous blood flowing into inlet chamber 7 and the pump outflow accumulates in CSC 14 via first access 15. Here diaphragm 13 moves towards third rigid wall 12; and air in air chamber 18 is expelled via air access 18c to accommodate the increasing blood volume. If venous blood flowing into inlet chamber 7 is lower than the flow arterial pump 20 generates, then the additional volume pumped by arterial pump 20 is withdrawn from CSC 14. The decrease in blood volume in CSC 14 causes diaphragm 13 to move towards second rigid wall 11 and air to enter air chamber 18 via air access 18c. This would continue until CSC 14 empties; air chamber 18 fills; and diaphragm 13 is sucked against second rigid wall 11, obstructing first access 15.

The higher first blood level h1 the larger area of screen 6 is available for venous blood flowing across screen 6 and the slower the blood velocity across each pore of screen 6. A slower velocity reduces the possibility of air bubbles entering inlet chamber 7 crossing screen 6 and exiting outlet 10 of first outlet chamber 9. A higher first blood level h1 also allows more time for air bubbles 7a to rise to first blood level h1 where they are removed. It is therefore advantageous to have first level h1 as high as possible. This is accomplished by assuring that first blood level h1, when venous blood is flowing into inlet chamber 7, is greater than second blood level h2 in CSC 14 and that that difference, third blood level h3, increases as the blood flow increases.

Since there is resistance to flow from the APC to CSC 14, blood level in inlet chamber 7, or outlet chamber 9, is always higher than blood level in the CSC 14, the difference, third blood level h3, is shown in FIG. 3a, the greater flow out of outlet chamber 9 the higher third blood level h3. This means that a larger area of screen 6 is available for blood flowing across screen 6 and that CSC 14 empties before outlet chamber 9. To avoid accidental emptying of outlet chamber 9, whereupon air would fill arterial pump 20, level detector 1a is attached to vertical wall 1 between first bottom 2 and first top 3. When triggered, level detector 1a causes pump 20 to either slow down or stop. Third blood level h3 can be decreased by reducing the resistance to flow between first outlet 10 and CSC 14, e.g., by increasing the internal diameter of conduit 16. Likewise, third blood level h3 can be increased by increasing the resistance to flow between first outlet 10 and CSC 14 by decreasing the internal diameter of conduit 16. The level detector is prior art.

As stated above, the primary innovation of the present HVR over Tamari's earlier U.S. patents '812, '440 and '696 is to provide a venous reservoir with a large volume capacity but small blood-air interface as taught in those patents but with a lower prime volume, lower operating volume and the ability to completely drain the blood remaining in the reservoir at the end of the case. This is achieved by combining the APC with CSC 14 wherein, the blood-air interface is limited to that of the first cross sectional area A1 of the APC. Thus, the larger the volume capacity of CSC 14 relative to the volume of the APC the smaller the blood-air interface 4 at height h1 relative to the total volume capacity of the present HVR (i.e., the volume capacity of the APC+ volume capacity of CSC 14). The volume capacity of CSC 14 should at least equal the volume of the APC but preferably greater than 2.5 times larger.

In the present embodiment blood is pulled directly from the APC by arterial pump 20. This change reduces the volume required to prime the system and allows for complete emptying of the reservoir at the end of the case. In Tamari's earlier patents, the HVR cannot empty completely, volume is retained in the fluid communication 4b in inlet 5 and outlet 6 as illustrated by line B-B' in FIG. 1b.

An embodiment for a typical adult sized HVR has a nominal internal cross-sectional area of outlet chamber 9 elliptical in shape with a major radius, a minor radius and a height of 5.0 cm, 1.8 cm and 15 cm respectively. These dimensions provide an APC with a nominal volume capacity of 420 ml and a maximum blood-air interface area A1 of 28 cm$^2$. CSC 14, spherical in shape, having a radius of 7.0 cm, has a nominal volume capacity of 1,400 ml, or 3.3 times larger than the volume capacity of the APC, (CSC 14 volume capacity)/(APC volume capacity). Thus, the HVR has a total nominal volume capacity of 1,800 ml but with the very low blood-air interface area of the APC lower than 30 cm$^2$.

Figure 4A:
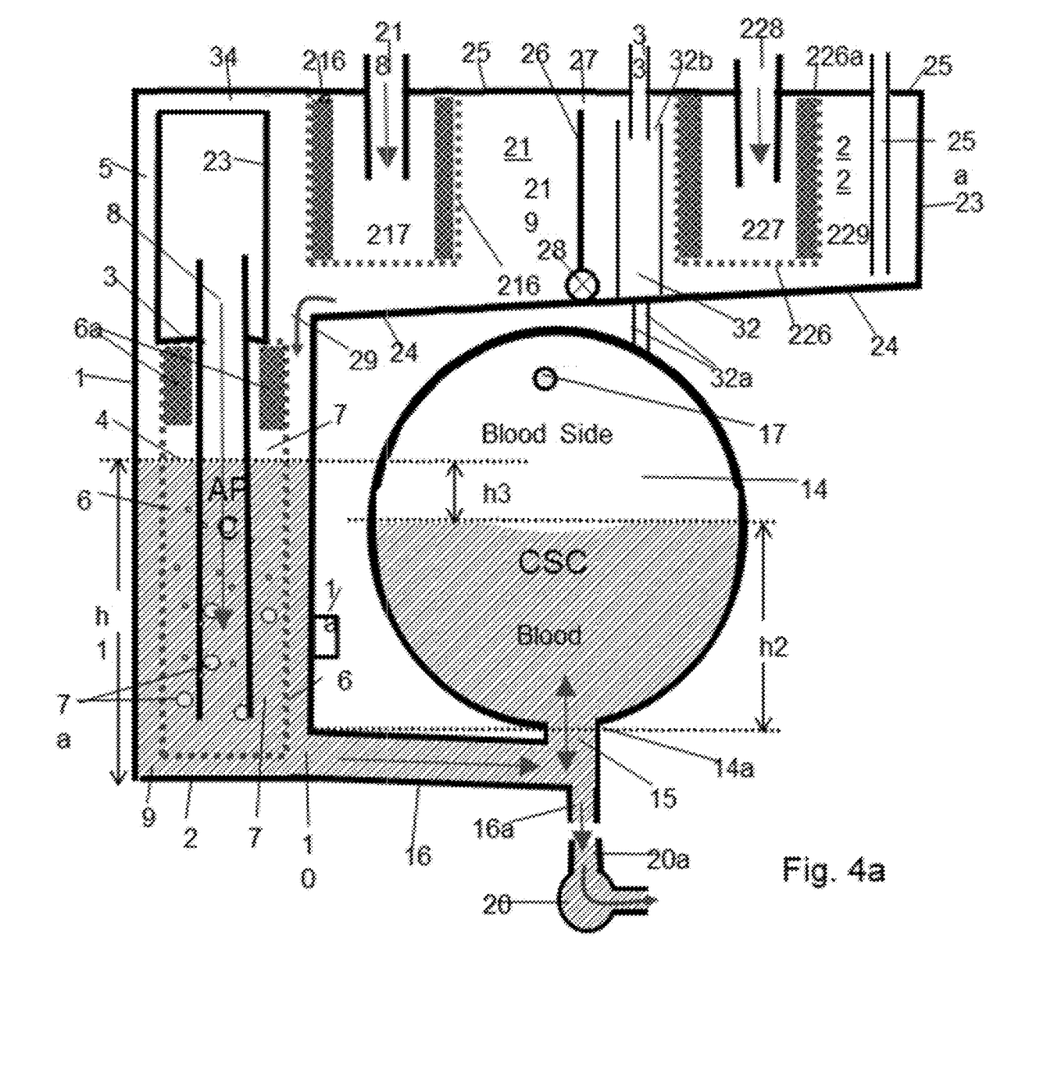
FIG. 4a is a line drawing of the present HVR illustrating a front view of the air purging chamber and the compliant storage chamber in combination with a two-chamber cardiotomy reservoir.
Figure 4B:
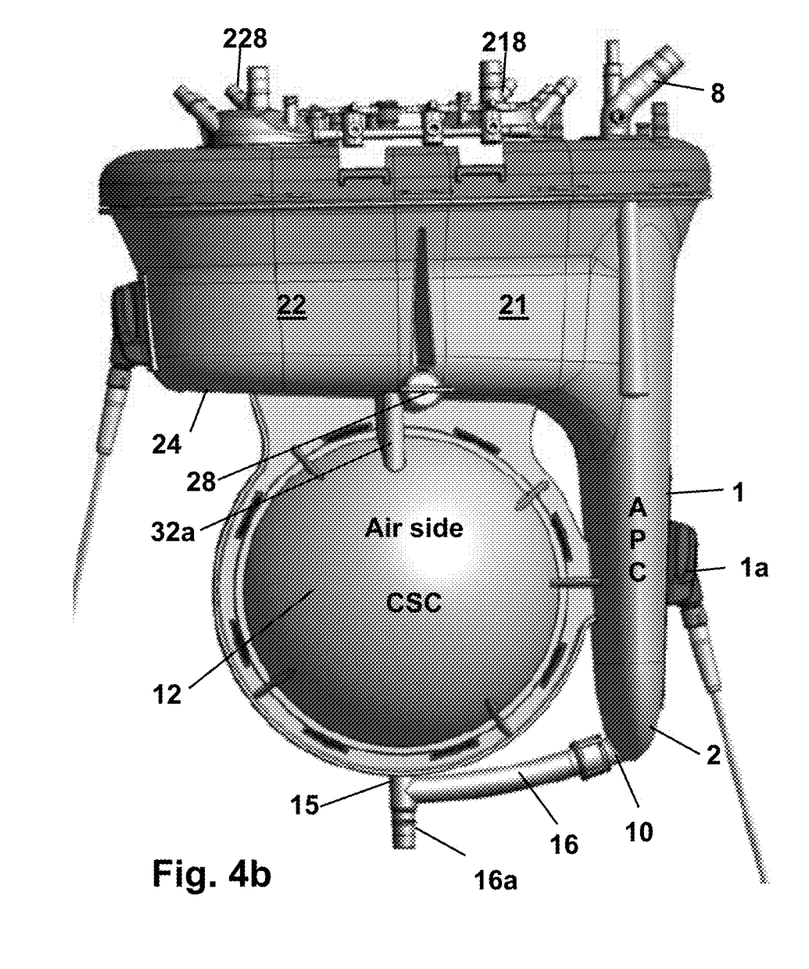
Figure 4C:
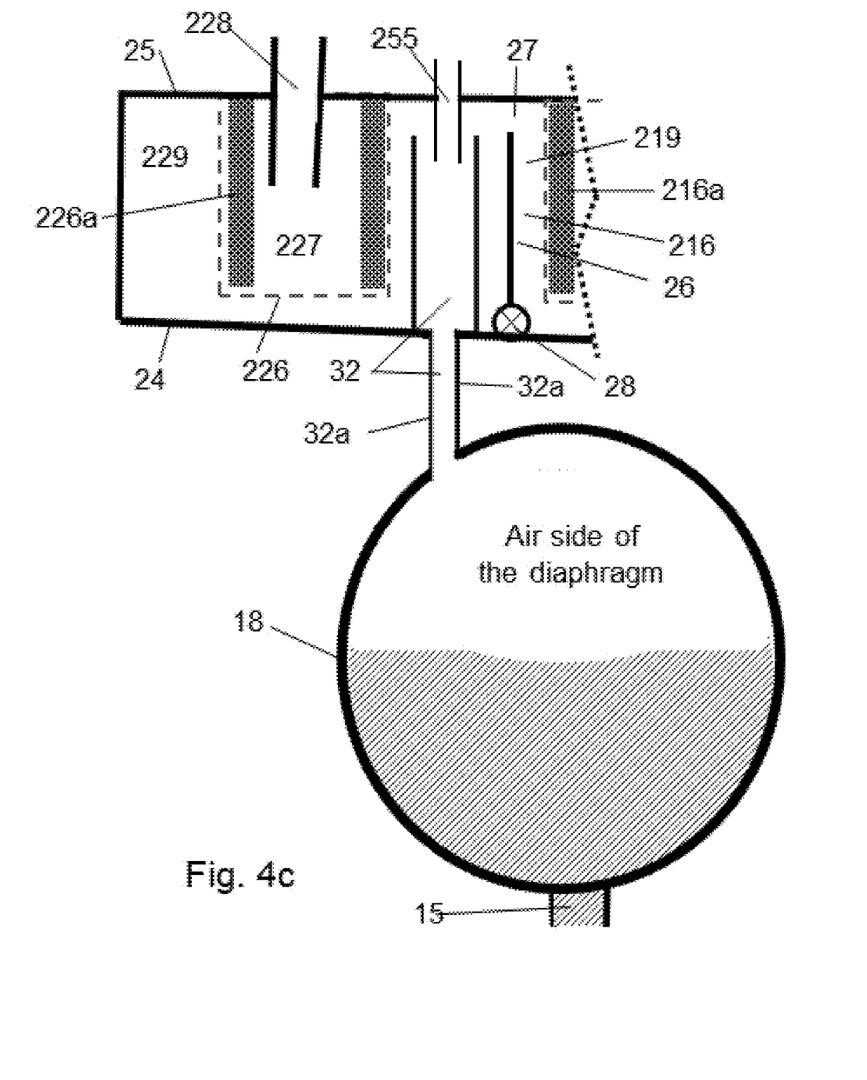
FIG. 4c is a line drawing illustrating a back view of the present HVR shown in FIG. 4a emphasizing a view of the vapor trap.

As described in details by Tamari's U.S. Pat. Nos. 7,591,812, 8,147,440, and 8,882,696, HVRs should handle "clean" and "dirty" blood separately. To that end, FIGS. 4a and 4b illustrate the present HVR, described in reference to FIGS. 3a and 3b, incorporating a two-chamber cardiotomy: "clean" blood chamber 21 and "dirty" blood chamber 22. The two chambers are formed by a common continuous fourth vertical rigid wall 23, common bottom 24, common top 25 and shared vertical wall 26. Shared vertical wall 26 extends upwards from fourth bottom 24 to just below fourth top 25 leaving first gap 27. Gap assures that the air pressure in dirty chamber 22 is the same as the air pressure in clean chamber 21. Common bottom 24 is slightly inclined so blood in the two-chambers flows towards third outlet 29 located along fourth bottom 24. Third outlet 29 provides liquid communication between clean chamber 21 and outlet chamber 9, but preferably with inlet chamber 7, through which blood entering chamber 21 combines with the venous blood in the APC.

Dirty chamber 22 filters and deaerate sucker blood flowing into it via dirty inlet port 228. It has dirty screen 226 and dirty defoamer 226a, the top which are attached to the underside of common wall 25, the combination forming an enclosed dirty inlet chamber 227. The dirty blood is defoamed by dirty defoamer 226a and is filtered by passing through dirty screen 226 into dirty outlet chamber 229.

Because of concerns for the inflammatory response associated with the dirty blood, the dirty blood is preferably stored in dirty outlet chamber 229 from where it can be withdrawn via tube 25a for processing. When valve 28, located at the bottom of common wall 26, is closed then dirty blood accumulates in chamber 22 from where it can be directed to a cell saver (not shown) for processing. Opening valve 28 forms a fluid communication between dirty chamber 22 and clean chamber 21 allowing the filtered dirty blood to flow into clean chamber 21 and from there combine with the venous blood in the APC via third outlet 29.

Clean chamber 21 separates and defoams clean blood flowing into it via clean inlet port 218. Clean chamber 21 includes clean screen 216 and third defoamer 216a, the two forming an enclosed clean inlet chamber 217 the top of which is attached to the underside of third top 25. Clean blood flowing into clean inlet chamber 217 is deaerated and defoamed with clean screen 216 and clean defoamer 216a respectively. The filtered clean blood flows into clean outlet chamber 219 and combines with the venous blood via outlet 29. Should the volume of the APC or CSC 14 fill up to capacity, then the excess venous blood can overflow into the clean chamber 21 as well as into dirty chamber 22.

It should be noted that clean chamber 21 and dirty chamber 22 provide additional volume capacity to the HVR. It should be obvious that once the venous blood reaches either or both clean chamber 21 and dirty chamber 22, then the blood-air interface increases to correspond to the cross-sectional area of those chambers.

The preferable nominal volume capacity for an adult patient of clean chamber 21 and dirty chamber 22 are 1,400 ml and 1,400 ml respectively providing a total nominal volume capacity for the HVR with the dual cardiotomy of 4,600 ml. When valve 28 is closed the HVR provides a nominal volume 3,200 ml prior to the venous/clean blood contacting the filter of dirty chamber 22.

As described in detail by Tamari's U.S. patents '812, '440, and '696, during VAVD it is necessary to trap water vapor in the air exhausted from the HVR that condenses on the cooler walls of the vacuum tubing (not shown) to prevent the condensate from dripping back into the blood. FIGS. 4*a* and 4*b* show vapor trap chamber 32 comprised of a sixth rigid vertical wall 32*a* forming a vertical chamber extending upward from second top 18*b* of air chamber 18 to dirty chamber 22 to just below common top 25 forming a fluid communication between air chamber 18 and dirty chamber 22. Second air exhaust 33, open at each end, is located along common top 25 with preferably, one open end extending below top 25 into the open end of vapor trap 32. The outside diameter of second air exhaust 33 is smaller than the internal diameter of vapor trap 32 leaving second gap 32*b*. The other open end of second air exhaust 33 extends above common top 25 forming a connector to connect to a regulated vacuum source (not shown) for VAVD applications or is open to ambient atmosphere. With this design the vapor trap chamber also serves as the fluid communication between the second air exhaust port 33 and air chamber 18.

To assure the HVR in combination with the two-chamber cardiotomy operates seamlessly, the air pressure in each of the chambers of that combination must be the same. To that end, vacuum applied to second exhaust port 33 is transmitted to air chamber 18 via vapor trap 32, dirty chamber 22 and via first gap 27 to clean chamber 21. Fluid communication 34 between clean chamber 21 and the APC assures that the air pressure in the APC is the same as the pressure in the other chambers. When second exhaust port 33 is open to ambient atmosphere, then the air pressure in all the above chambers is at atmospheric pressure. This design assures unhindered fluid communication between the air in dirty chamber 22, vapor trap 32, clean chamber 21, the APC and CSC 14 (via air chamber 18).

FIG. 4*b* is a 3-D rendition of the exterior of one rendition of an HVR described in FIG. 4*a*. Shown are the APC; CSC 14; level detector 1*a*; first bottom 2 of the APC; first inlet 8; first outlet 10; third rigid wall 12 forming air chamber 18; first access 15 to CSC 14; conduit 16, preferably being tubular, forming fluid communication between the APC and CSC; outlet port 16*a* that forms a fluid communication with pump 20; clean chamber 21 of the two-chamber cardiotomy; dirty chamber 22 of the of the two-chamber cardiotomy; common bottom 24 of the two-chamber cardiotomy; valve 28 between dirty chamber 22 and clean chamber 21; sixth rigid vertical wall 32*a* that forms part of the vapor trap and provides a fluid communication between air chamber 18 and dirty chamber 22; dirty inlet 228 to dirty chamber 22; and clean inlet 218 to clean chamber 21.

It should be understood that the aforementioned specifications are given for adult patients with expected blood flow between 4 and 7 L/min, can be scaled down to accommodate lower flows associated with smaller patients by retaining the volume capacity of CSC 14 to be at least as large as the volume capacity of the APC but preferably at least twice that of the APC.

It should be understood that a comprehensive description of each of the embodiments of the present HVR is beyond the scope of a patent application and therefore the aforementioned descriptions are given as illustrations and should not be used to limit the intent, spirit or scope of the invention.

I claim:

1. A hybrid venous reservoir for storing venous blood of a patient undergoing cardiopulmonary bypass with a pump that generates blood flow; the pump having a pump inlet, the hybrid venous reservoir being configured to trap and remove air bubbles from venous blood entering it and provide volumetric compliance, the hybrid venous reservoir comprising:
   a) an air purging chamber defined by at least a first vertical wall, a first bottom and a first top, the air purging chamber being configured to contain blood and air wherein an interface between the blood and air (blood-air) occurs at a first height from the first bottom, the air purging chamber having a first horizontal cross-sectional area at the first height; the air purging chamber comprising:
      i) a first air exhaust port along the first top providing fluid communication with ambient atmosphere;
      ii) a screen dividing the air purging chamber into:
         (1) an inlet chamber having a first inlet;
         (2) a first outlet chamber having a first outlet;
      iii) a fluid communication between the first inlet and the first outlet provided by the screen, the screen being configured to hinder air bubbles entering the inlet chamber from reaching the first outlet, the air bubbles rising to the first height from where the air bubbles are purged to ambient atmosphere via the first air exhaust port;
      iv) a fluid communication between the inlet chamber and the first outlet chamber such that pressures in the inlet chamber and the first outlet chamber are the same and that air in either the inlet chamber and first outlet chamber can be exhausted via the first air exhaust port;
      v) a first volume capacity and a blood level in the in the air purging chamber defined by a first vertical height from the first bottom;
   b) a dual chamber adapted to contain venous blood comprising:
      i) a second rigid wall and a third rigid wall;
      ii) a diaphragm having a pliable wall, the diaphragm having a blood side and an air side, said diaphragm being sandwiched and sealed between the second rigid wall and the third rigid wall thereby forming a compliant storage chamber and an air chamber:
         (1) wherein the compliant storage chamber, formed by the second rigid wall and the blood side of the diaphragm, comprising:
            (a) a second bottom;
            (b) a second top;
            (c) a first access to the compliant storage chamber located along the second bottom;
            (d) a port located along the second rigid wall of the compliant storage chamber;
            (e) a conduit forming a fluid communication between the first outlet of the air purging chamber and the compliant storage chamber via the first access; and
            (f) a second volume capacity, wherein a blood level in the compliant storage chamber is defined by a second vertical height from the second bottom;
         (2) wherein the air chamber, formed between the third rigid wall and the air side of the diaphragm, comprising:
            (a) a third top;
            (b) a third bottom;

(c) an air access incorporated into the third rigid wall, in fluid communication with the air chamber; and
    (3) a second outlet, incorporated in the conduit in fluid communication with the first outlet and first access, that can connect to the inlet of the pump;
  c) a fluid communication between the first air exhaust port of the air purging chamber and the air access of the air chamber that assures the air pressure in the compliant storage chamber and the air chamber is equal whether the first air exhaust port is open to ambient atmosphere or is adopted to accommodate a tube connected to a regulated vacuum source to allow vacuum assisted venous drainage (VAVD);
wherein the blood-air interface of the hybrid venous reservoir is limited to that of the first horizontal cross-sectional area of the air purging chamber.

2. The hybrid venous reservoir of claim 1, wherein the port located along the second rigid wall is configured to withdraw/expel air in the compliant storage chamber.

3. The hybrid venous reservoir of claim 1, wherein the second outlet is formed to accept a tubing that can be connected to inlet of the pump.

4. The hybrid venous reservoir of claim 1, wherein the pliable diaphragm is compatible with blood and is made thin enough and pliable enough to assure that the pressure in the complaint storage chamber and the pressure in the air chamber are within 5 mmHg of each other.

5. The hybrid venous reservoir of claim 1, wherein a periphery of the diaphragm is configured to form the seal between the blood side of the diaphragm and the second rigid wall forming the compliant storage chamber.

6. The hybrid venous reservoir of claim 1, wherein a periphery of the diaphragm is configured to form the seal between the air side of the diaphragm and the third rigid wall forming the air chamber.

7. The hybrid venous reservoir of claim 1, wherein a size of the hybrid venous reservoir is selected based on the size of the patient.

8. The hybrid venous reservoir of claim 1, further comprising a defoaming means for defoaming the venous blood entering the air purging chamber.

9. The hybrid venous reservoir of claim 1, further comprising a structure that includes a cardiotomy reservoir having a clean chamber and a dirty chamber, the clean chamber and the dirty chamber comprising:
  i) a common vertical wall;
  ii) a common top having an underside;
  iii) a common bottom;
  iv) a shared vertical wall having a first side and a second side and a top, the shared wall extending upward from the common bottom with the first side defining one wall of the clean chamber and the second side defining one wall of the dirty chamber;
  v) a valve incorporated along the common bottom and the shared vertical wall, the valve, when open, forming a fluid communication along the common bottom between the clean chamber and the dirty chamber;
  vi) a gap, between the top of the shared vertical wall and the underside of the common top, forming a fluid communication between the clean chamber and the dirty chamber along the common top, the gap providing a fluid communication assuring the air pressures in the clean chamber and the dirty chamber are the same;
  vii) a second air exhaust port, located along the common top in fluid communication with ambient atmosphere or connected to a regulated vacuum source for VAVD;
  viii) the clean chamber configured to deaerate and defoam clean blood comprising:
    (1) a clean filter forming a wall, defining a clean inlet chamber, attached to the underside of the common top;
    (2) a clean defoamer inside the clean inlet chamber;
    (3) a clean inlet port accepting and directing clean blood into the clean inlet chamber; and
    (4) a clean outlet chamber formed between the clean filter, the common vertical wall, the common top, the first side of the shared wall and the common bottom; and
  ix) the dirty chamber configured to filter, deaerate and defoam dirty blood comprising:
    (1) a dirty filter forming a wall defining a dirty inlet chamber attached to the underside of the common top;
    (2) a dirty defoamer inside the inlet dirty chamber;
    (3) a dirty inlet port directing dirty blood into the dirty inlet chamber; and
    (4) a dirty outlet chamber formed between the dirty filter, the common vertical wall, the common top, the second side of the shared wall and the common bottom.

10. The hybrid venous reservoir of claim 1, further comprising a structure having at least a sixth rigid wall forming a vapor trap chamber and a fluid communication between the second air exhaust port and the air chamber.

11. The hybrid venous reservoir of claim 1, further comprising a fluid path along the first top forming a direct fluid communication between the first outlet chamber and the first air exhaust port.

12. A hybrid venous reservoir for storing venous blood of a patient undergoing cardiopulmonary bypass with a pump that generates blood flow; the pump having a pump inlet, the hybrid venous reservoir being configured to trap and remove air bubbles from venous blood entering it and provide volumetric compliance, the hybrid venous reservoir comprising:
  a) an air purging chamber defined by at least a vertical wall, the air purging chamber being configured to contain blood and air having an interface between the blood and air (blood-air), the air purging chamber having a first horizontal cross-sectional area at the blood-air interface: the air purging chamber comprising:
    i) a first air exhaust port providing fluid communication with ambient atmosphere;
    ii) a screen dividing the air purging chamber into:
      (1) an inlet chamber having a first inlet,
      (2) a first outlet chamber having a first outlet;
    iii) a fluid communication between the first inlet and the first outlet provided by the screen, the screen being configured to hinder air bubbles entering the inlet chamber from reaching the first outlet;
    iv) a first volume capacity;
  b) a dual chamber adapted to contain venous blood comprising:
    i) a first rigid wall and a second rigid wall;
    ii) a diaphragm having a pliable wall, the diaphragm having a blood side and an air side, said diaphragm being sandwiched and sealed along its periphery between the first rigid wall and the second rigid second wall thereby forming a compliant storage chamber and an air chamber:

(1) wherein the compliant storage chamber is formed by the first rigid wall and the blood side of the diaphragm, the compliant storage chamber comprising:
 (a) a first access to the compliant storage chamber;
 (b) a conduit providing fluid communication between the air purging chamber via the first outlet and the compliant storage chamber via the first access; and
 (c) a second volume capacity;
(2) wherein the air chamber is formed between the second rigid wall and the air side of the diaphragm, the air chamber comprising:
 (a) an air access incorporated into the second rigid wall in fluid communication with the air chamber; and
(3) a second outlet incorporated in the conduit providing fluid communication between the first outlet chamber and the access to the compliant storage chamber, the second outlet designed to connect to the pump
c) a fluid communication between the first air exhaust port of the air purging chamber and the air access to the air chamber that assures the air pressures in the compliant storage chamber and the pressure in the air chamber are equal whether the air exhaust port is open to ambient atmosphere or is adopted to accommodate a tube connected to a regulated vacuum source to allow vacuum assisted venous drainage (VAVD);
wherein area of the blood-air interface of the hybrid venous reservoir is limited to that of the first horizontal cross-sectional area of the air purging chamber.

13. The hybrid venous reservoir of claim 1, wherein the second volume capacity is at least equal to the first volume capacity.

14. The hybrid venous reservoir of claim 12, wherein the second volume capacity is at least equal to the first volume capacity.

15. The hybrid venous reservoir of claim 1, such that when venous blood flows into the inlet chamber the first vertical height is higher than the second vertical blood height availing a larger section of the screen for blood to cross from the inlet chamber to the first outlet chamber, the larger section of the screen resulting in a lower blood velocity crossing the screen thereby reducing the possibility of air bubbles entering the inlet chamber from crossing the screen into the first outlet chamber.

16. The hybrid venous reservoir of claim 12, such that when venous blood flows into the inlet chamber the first vertical height is higher than the second vertical blood height availing a larger section of the screen for blood to cross from the inlet chamber to the first outlet chamber, the larger section of the screen resulting in a lower blood velocity crossing the screen thereby reducing the possibility of air bubbles entering the inlet chamber from crossing the screen into the first outlet chamber.

17. The hybrid venous reservoir of claim 1 wherein the first outlet is vertically above the second outlet such that the fluid communication between the outlet of the air purging chamber and the compliant storage chamber is on a slight down incline towards the second outlet.

18. The hybrid venous reservoir of claim 12 wherein the first outlet is vertically above the first outlet port such that the fluid communication between the outlet of the air purging chamber and the compliant storage chamber is on a slight down incline towards the second outlet.

19. The hybrid venous reservoir of claim 12, wherein a size of the hybrid venous reservoir is selected based on the size of the patient.

\* \* \* \* \*